United States Patent
Toki et al.

(10) Patent No.: US 7,492,967 B2
(45) Date of Patent: Feb. 17, 2009

(54) SUPER-RESOLUTION PROCESSOR AND MEDICAL DIAGNOSTIC IMAGING APPARATUS

(75) Inventors: Yuusuke Toki, Tokyo (JP); Yasuko Fujisawa, Otawara (JP); Motoshi Kato, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 568 days.

(21) Appl. No.: 10/946,247

(22) Filed: Sep. 22, 2004

(65) Prior Publication Data

US 2005/0063611 A1    Mar. 24, 2005

(30) Foreign Application Priority Data

Sep. 24, 2003   (JP)   ............................ 2003-332192
Sep. 24, 2003   (JP)   ............................ 2003-332193

(51) Int. Cl.
G06K 7/00       (2006.01)
A61B 8/00       (2006.01)
(52) U.S. Cl. .................. 382/299; 382/312; 600/443
(58) Field of Classification Search ......... 382/131–132, 382/254, 298–300, 305, 312; 378/4, 14, 378/19; 600/443
See application file for complete search history.

(56) References Cited

U.S. PATENT DOCUMENTS

| 5,128,864 | A  | * | 7/1992  | Waggener et al. | ............. 378/14 |
| 5,335,255 | A  | * | 8/1994  | Seppi et al.    | .................... 378/4 |
| 5,383,457 | A  | * | 1/1995  | Cohen           | ........................ 600/443 |
| 5,960,058 | A  |   | 9/1999  | Baba et al.     | |
| 6,218,673 | B1 | * | 4/2001  | Gore et al.     | ............... 250/474.1 |
| 6,278,767 | B1 |   | 8/2001  | Hsieh           | |
| 6,366,638 | B1 | * | 4/2002  | Hsieh et al.    | .................... 378/19 |
| 6,434,280 | B1 | * | 8/2002  | Peleg et al.    | ................. 382/299 |
| 6,459,823 | B2 | * | 10/2002 | Altunbasak et al. | ......... 382/299 |
| 6,907,102 | B1 | * | 6/2005  | Sauer et al.    | .................... 378/19 |
| 6,928,182 | B1 | * | 8/2005  | Chui            | ......................... 382/131 |
| 7,105,824 | B2 | * | 9/2006  | Stoddart et al. | ........ 250/363.04 |

FOREIGN PATENT DOCUMENTS

| JP | 11-342132    | 12/1999 |
| JP | 2000-350728  | 12/2000 |
| WO | WO 00/22573  | 4/2000  |

* cited by examiner

*Primary Examiner*—Kanji Patel
(74) *Attorney, Agent, or Firm*—Oblon, Spivak, McClelland, Maier & Neustadt, P.C.

(57) ABSTRACT

A super-resolution processor includes a storage section for storing data of point spread functions of an X-ray CT scanner which are acquired using a phantom and a super-resolution processing section performing super-resolution of image data of a sample generated by the X-ray CT scanner using the stored point spread functions.

12 Claims, 11 Drawing Sheets

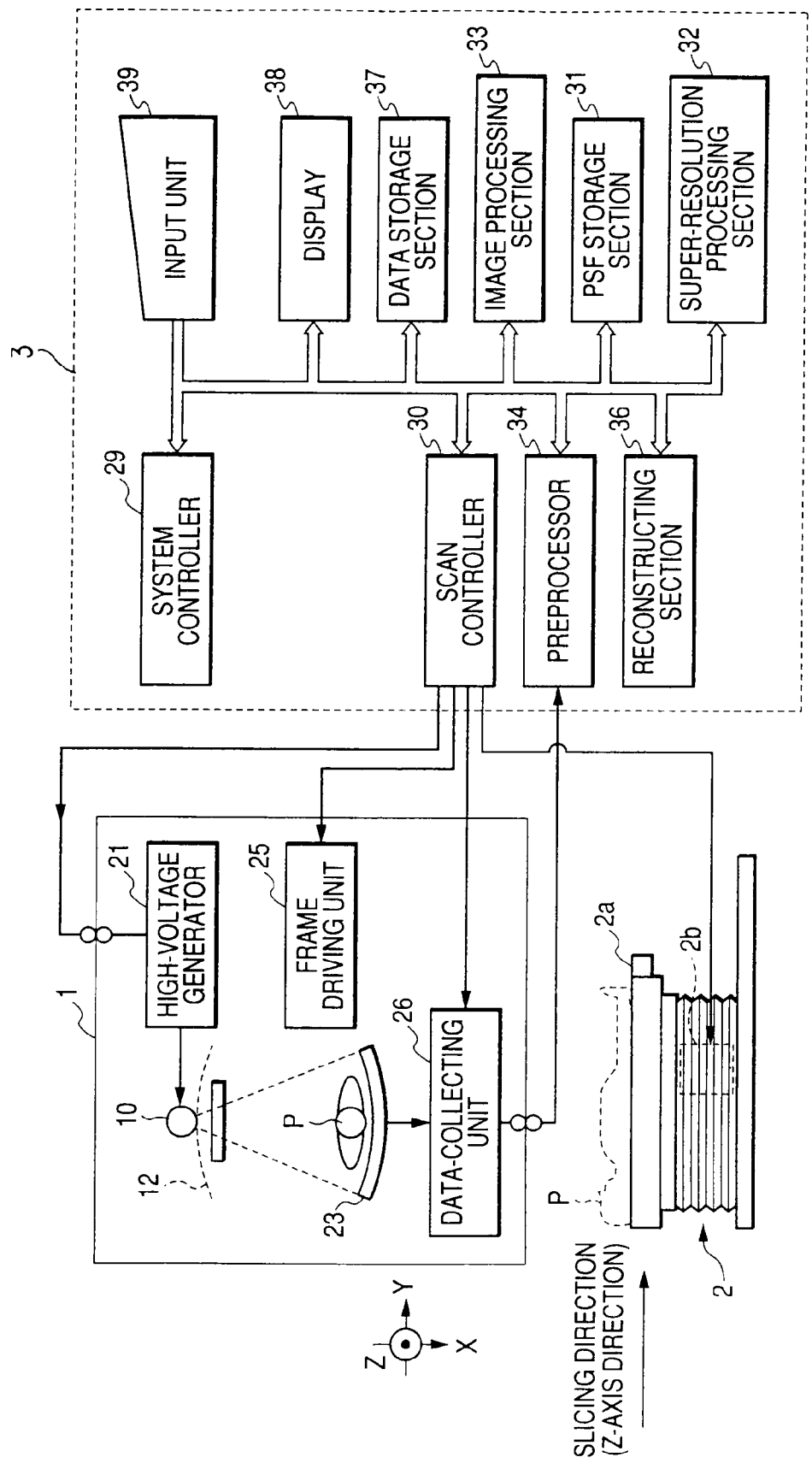

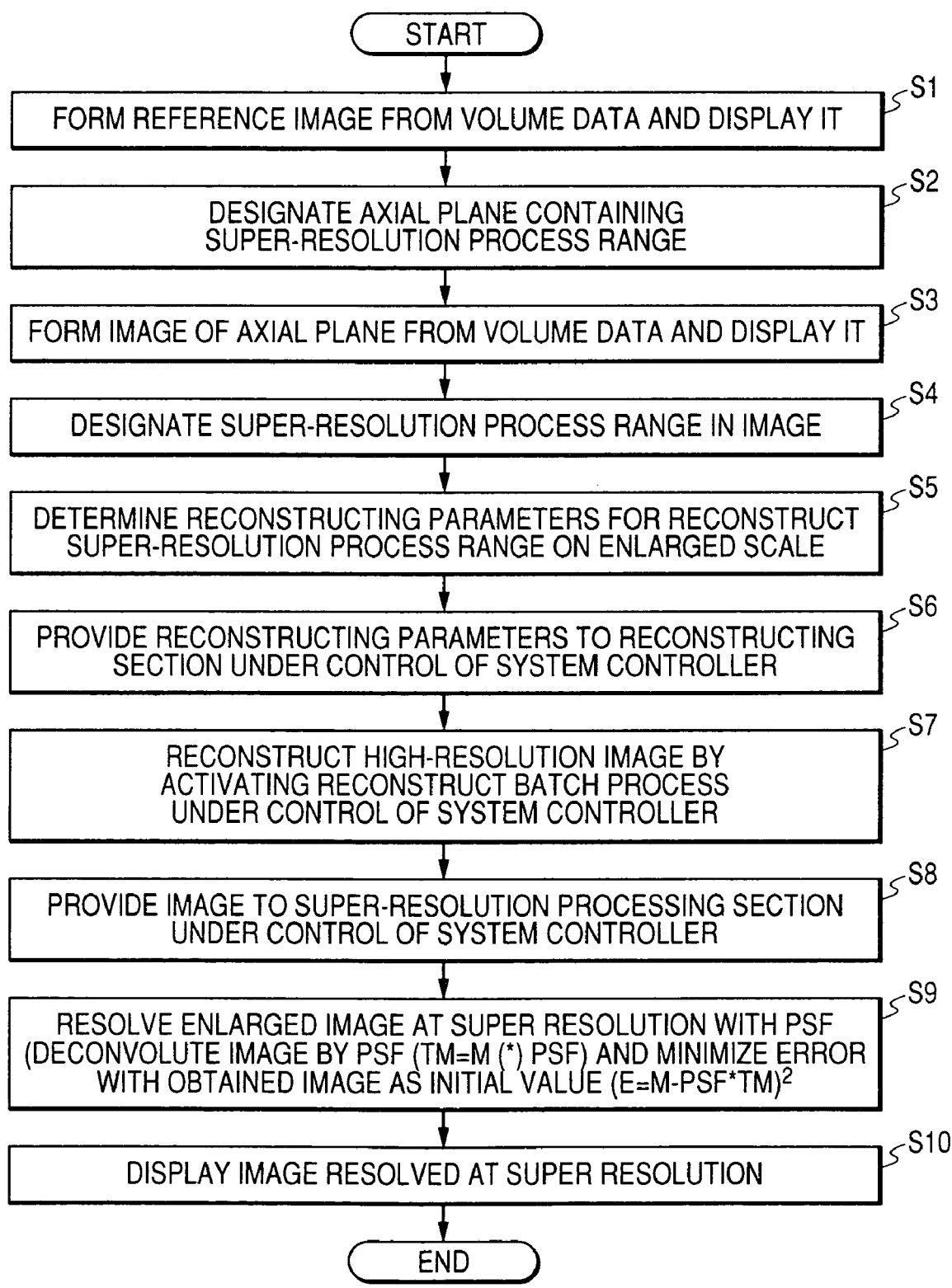

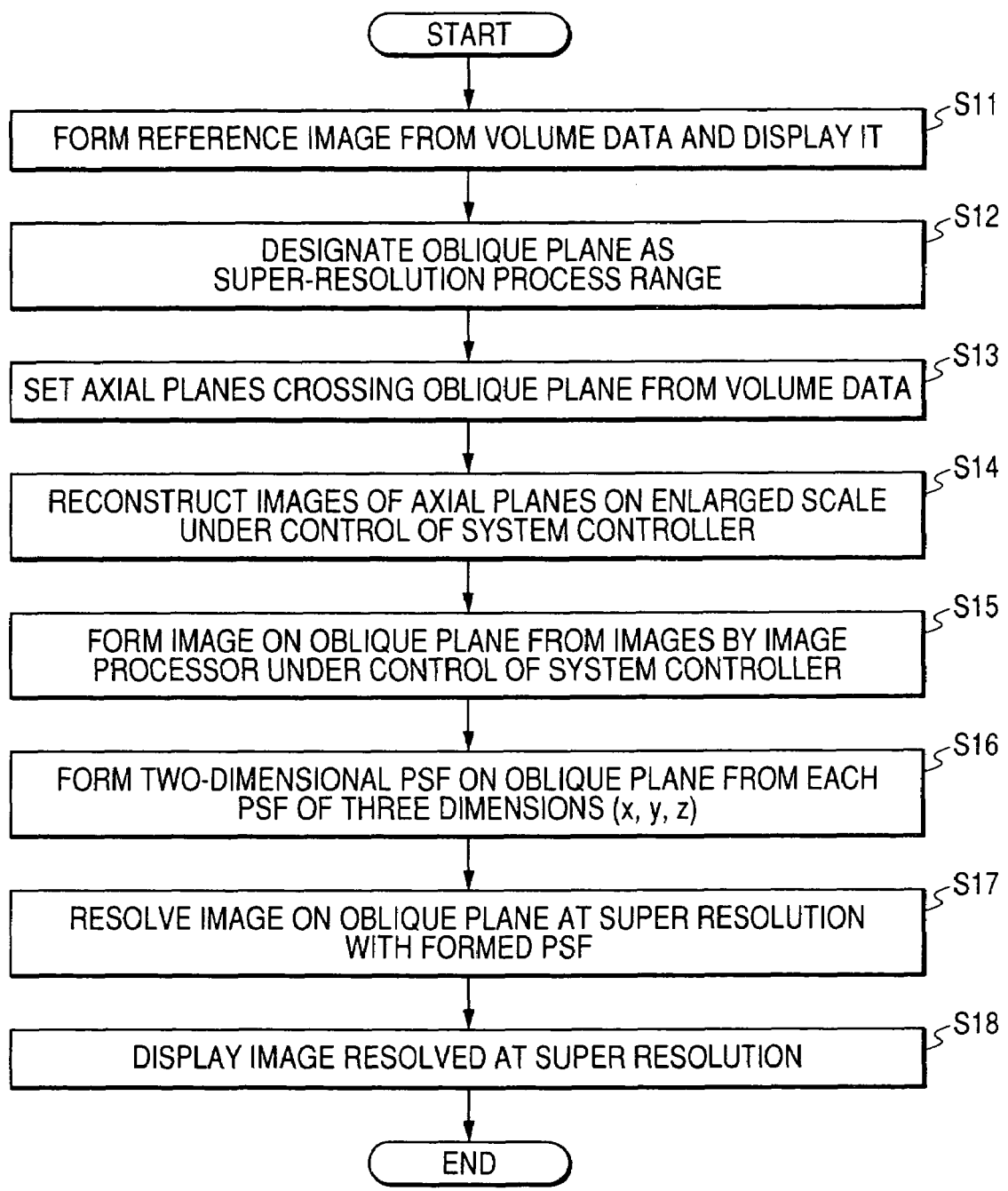

SETTING AXIAL IMAGES

CONCEPTUAL DIAGRAM OF
THREE-DIMENSIONAL
PSF (BLURRING) FUNCTION

X-, Y-DIRECTION

Z-DIRECTION

3DR01

SETTING AXIAL
IMAGES CONTAINING
PROCESS RANGE

MIMIC BLOOD VESSEL

MEASUREMENT IMAGE

SUPER-RESOLVED IMAGE

SUPER-RESOLUTION PROCESSOR AND MEDICAL DIAGNOSTIC IMAGING APPARATUS

CROSS-REFERENCE TO RELATED APPLICATIONS

This application is based upon and claims the benefit of priority from prior Japanese Patent Applications No. 2003-332192, filed Sep. 24, 2003; and No. 2003-332193, filed Sep. 24, 2003, the entire contents of both of which are incorporated herein by reference.

BACKGROUND OF THE INVENTION

1. Field of the Invention

The present invention relates to a super-resolution processor and a medical diagnostic imaging apparatus for performing super-resolution processing on volume data or multislice data collected by an X-ray CT scanner.

2. Description of the Related Art

X-ray CT scanners have made considerable progress and, in response to strong demand for higher-definition (higher-resolution) imaging from a medical field, multislice X-ray CT scanners have recently been developed and become widely available. The multislice X-ray CT scanner includes an X-ray source for emitting fan-beam X-rays having a broadening width in a slicing direction (along the base) and a two-dimensional detector with a structure in which multiple rows (four, eight, sixteen, etc.) of detecting elements are arrayed in the slicing direction, which are operated by multiscanning or helical scanning. This provides high-accuracy volume data across the wide range of a sample in a short time as compared with a single-slice X-ray CT scanner.

The volume data obtained in such a way is recently not only displayed for observation but also used in various applications. For example, for medical use, it is used for measuring the ratio of angiostenosis, aneurysm, or varicose veins. Specifically, an X-ray contrast medium is given to a sample for imaging by an X-ray CT scanner, so that volume data can be provided in which the distribution of the contrast medium flowing in the blood vessel is imaged. Accordingly, the ratio of angiostenosis and the size of aneurysm or varicose veins can be measured from the distribution of the CT value of the contrast medium imaged in the volume data. For example, the ratio of angiostenosis is obtained by measuring the thickness of the inner wall of the blood vessel (the range occupied by the contrast medium) from the volume data and comparing the thickness of an apparently normal region of the blood vessel to that of a thin region. For the measurement of the thickness of a blood vessel, a threshold for a CT value is generally set.

JP-A-11-342132 discloses another example of the process of volume data acquired from not only the X-ray CT scanner but various medical imaging scanners including an ultrasonic diagnostic imaging scanner and a magnetic resonance imaging scanner. The scanners described in JP-A-11-342132 are intended for accurate blood-vessel measurement based on display images, wherein a region of interest is set that crosses the wall of a blood vessel vertically on the tomogram of the vessel and the size of the vessel is measured from the profile of the pixel values in that region. JP-A-2000-350726 describes another example intended for accurate measurement of the length of a region of interest (a blood vessel, bowels, etc.) having curvature in a direction that is not in parallel to the projection plane using a maximum intensity projection (MIP) image.

Not only the X-ray CT scanner but also all imaging scanners have resolution limit that depends on the pitch of the detecting elements of their detectors. Referring to FIG. 11, particularly, the CT image of the X-ray CT scanner is formed as a reverse projection sum of a large number of views. Accordingly, blurring that depends on the resolution limit appears on the image as a result of multidirectional multiple combination of data profiles of one view at a minute point. In other words, the CT image can be stated as the intensity distribution function of a minute point image which represents blurring, that is, the assembly of point spread functions (PSFs).

However, no consideration is given to the blurring under present circumstances.

BRIEF SUMMARY OF THE INVENTION

It is an object of the present invention to make super-resolution of medical images commercially practical.

A super-resolution processor according to a first aspect of the invention includes a storage section for storing data of point spread functions of an X-ray CT scanner which are acquired using a phantom, and a super-resolution processing section performing super-resolution of image data of a sample generated by the X-ray CT scanner using the stored point spread functions.

A super-resolution processor according to a second aspect of the invention includes means for storing projection data of a sample acquired by an X-ray CT scanner, means for designating a super-resolution process range on a three-dimensional image of the sample, means for reconstructing image data from the projection data only in the designated super-resolution process range, and means for performing super resolution of the reconstructed image data using point spread functions for the X-ray CT scanner.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a schematic block diagram of an X-ray CT scanner including a super-resolution processor according to an embodiment of the present invention;

FIG. 2 is a flowchart for a first super-resolution processing procedure according to the embodiment;

FIG. 4 is a flowchart for a second super-resolution processing procedure according to the embodiment;

DETAILED DESCRIPTION OF THE INVENTION

Figure 3A:
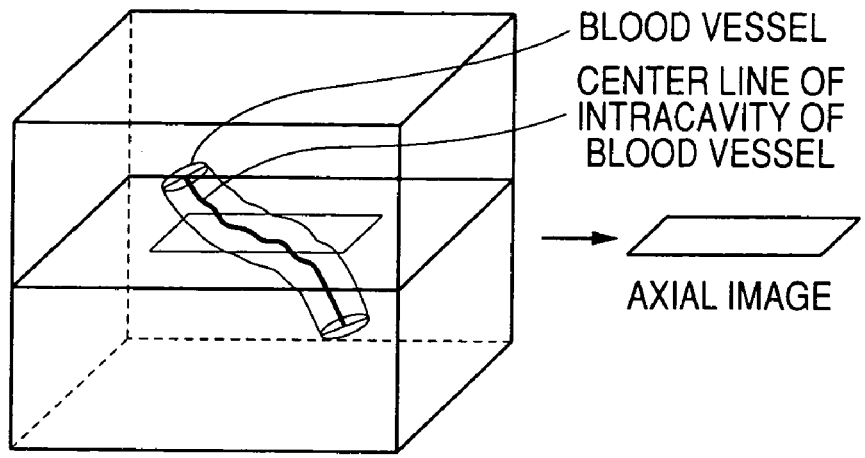
FIGS. 3A to 3E are supplementary diagrams of the first super-resolution processing procedure of FIG. 2.

A medical diagnostic imaging apparatus equipped with a super-resolution processor according to an embodiment of the present invention will be described hereinafter with reference to the drawings. Although an X-ray CT scanner will be described here as an example of the medical diagnostic imaging apparatus, the invention may be applied to another modality, such as a magnetic resonance imaging scanner (MRI scanner), an ultrasonic diagnostic imaging apparatus, a positron emission CT (PET) scanner, a single-photon emission CT (SPECT) scanner, a gamma camera, or an X-ray diagnostic apparatus.

The X-ray CT scanner includes various types: a rotation/rotation type which rotates around a sample in combination of an X-ray tube and a radiation detector, a fixed/rotation type in which a large number of detecting elements are arrayed in a ring shape and only an X-ray tube rotates around the sample, etc. Any types can incorporate the invention. Here a mainstream rotation/rotation type will be described. To reconstruct one-slice tomogram data, projection data of about 360°, or 180°+α (α: fan angle) for a half scanning method is required. The invention can be applied to both of the reconstruction methods. Here the half scanning method will be described by way of example. The dominating mechanism for converting incident X-rays to electrical charge includes indirect conversion in which X-rays are converted to light with a fluorescent substance such as a scintillator and the light is further converted to electrical charge by a photoelectric transducer such as a photodiode and direct conversion which uses generation of electron-hole pairs in a semiconductor by X-rays and their migration to an electrode, that is, a photoconductive phenomenon. Although the X-ray detecting element may be of either of the methods, here the former indirect conversion will be described by way of example. A so-called multitubular X-ray CT scanner in which multiple pairs of an X-ray tube and an X-ray detector are mounted on a rotation ring has become commercially available in recent years and so its peripheral techniques have been developed. The invention is applicable to both of the conventional single-tube X-ray CT scanner and the multitubular X-ray CT scanner. Here the single-tube type will be described.

Referring to FIG. 1, an X-ray CT scanner includes a frame 1 constructed so as to collect projection data of a sample. The frame 1 includes an X-ray tube 10 and an X-ray detector 23. The X-ray tube 10 and the X-ray detector 23 are mounted on a ring-shaped rotating frame 12 rotated by a frame driving unit 25. The center of the rotating frame 12 is open, into which a sample P placed on the top plate 2a of a base 2 is inserted. The rotation axis of the rotating frame 12 is defined as Z-axis (slicing-direction axis) and a plane perpendicular to Z-axis is defined as two axes, X and Y, orthogonal to Z-axis.

Tube voltage is applied between the negative electrode and the positive electrode of the X-ray tube 10. Filament current is applied to the filament of the X-ray tube 10 from a high-voltage generator 21. X-ray generates by the application of the tubular voltage and the filament current. The X-ray detector 23 may be any of a one-dimensional array type detector and a two-dimensional array type detector (also referred to as multislice type detector). The X-ray detecting element has a square acceptance surface of, e.g., 0.5 mm×0.5 mm. For example, 916 X-ray detecting elements are arrayed along the channel. For example, 40 parallel rows of arrays form a two-dimension array type detector. One array of elements forms a one-dimensional type array detector.

A data-collecting unit 26, which is generally called a data acquisition system (DAS), converts a signal outputted for each channel from the X-ray detector 23 to a voltage signal, and amplifies, and further converts it to a digital signal. The data (raw data) is supplied to a computing unit 3 disposed outside the frame. A preprocessor 34 of the computing unit 3 gives correction processing such as sensitivity correction to the data (raw data) outputted from the data-collecting unit 26 to output projection data. The projection data-is sent to a data storage section 37 of the computing unit 3 and stored therein.

The computing unit 3 includes the preprocessor 34, the data storage section 37, a system controller 29, a scan controller 30, a reconstructing section 36, a display 38, an input unit 39, a PSF storage section 31, a super-resolution processing section 32, and an image processing section 33. The reconstructing section 36 reconstructs image data on the basis of projection data collected by helical scanning, volume scanning with cone beam X-rays, or by the combined use of them.

The PSF storage section 31 stores data of point spread functions (PSF) for X-, Y-, and X-directions peculiar to the X-ray CT scanner in advance. Here the point spread function denotes a CT value. The PSF data is acquired as two-dimensional or three-dimensional data (out-of-focus image) of a wire phantom or a microsphere acquired by scanning a wire phantom of a diameter smaller than 0.5 mm, e.g., one-tenth thereof (0.05 mm), which is the pitch (resolution limit) of the X-ray detector 23, or a microsphere for three dimensions, and reconstructing its projection data, in this case, by reconstructing the region around the wire phantom or the microsphere on an enlarged scale. Briefly, PSF is obtained as enlarged image data of a reconstructed microobject of a size (diameter) less than the resolution limit.

The PSF data acquired from the wire phantom is measured in advance and stored in the PSF storage section 31. The PSF data is used in common in all samples. Since there is no need to acquire PSF data for each sample, the need for scanning for acquiring PSF data for each sample is eliminated. Therefore, exposure of samples to X-rays is reduced, thus allowing practical use.

The super-resolution processing section 32 resolves the image of an object at high resolution with the PSF data. Here an image reconstructed by the reconstructing section 36 on an enlarged scale is the object to be processed. It is also possible to enlarge an image cut out from volume data by multi planar reformatting (MPR) etc. by the image processing section 33, or increase the matrix size of the pixels, and use the image as object of super-resolution. In the super-resolution processing, the super-resolution processing section 32, the image processing section 33, and the reconstructing section 36 are operatively associated with one another in accordance with a predetermined process sequence under the control of the system controller 29. The super-resolution processing according to the embodiment includes first to third super-resolution processings, as will be described in sequence, a desired process of which is selected by an operator with the input unit 39.

Figure 3B:
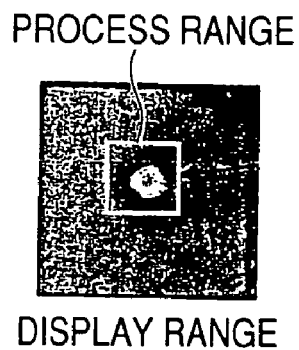

FIG. 2 shows the first super-resolution processing procedure according to the embodiment. In step S1, a reference image (three-dimensional image) is formed by the image processing section 33 from volume data or multislice data produced by volume-reconstruction of the three-dimensional region of a sample and is displayed on the display 38 (refer to FIG. 3A). When an axial plane perpendicular to Z-axis and containing a super-resolution process range is designated on the displayed reference image by the operator with the input unit 39 (S2), an image for the designated axial plane is generated from the volume data by the image processing section 33 and displayed (S3). In step S4, a narrower local range (super-resolution process range) containing a super-resolution object portion is designated on an image of the displayed axial plane by the operator with the input unit 39 (refer to FIG. 3B). Limiting the super-resolution process range as much as possible allows reconstruction of the image within the range (zooming) at extremely high resolution, which allows reconstruction (reconstruction on an enlarged scale with) expression of a gentle PSF curve. As well known, since the super-resolution processing includes the process of deconvoluting each of all pixels by PSF, the steps of process increase with the number of object pixels (matrix size). However, limiting the super-resolution process range as much as possible reduces processing time effectively, thus improving practical performance. Of course, when the limitation of process range is not required because of speedup of the processor, the entire initial reconstruction field of view (FOV) may be the object of the super-resolution processing. In that case, the image is reconstructed with the matrix size which is obtained by multiplying the range by an enlargement ratio (for example, for the display matrix with a size of 512×512 and the enlargement ratio of ×8, a 4096 by 4096 matrix of pixels), and then resolved at super resolution.

Then reconstruction parameters for reconstructing (zooming) the image of the circular reconstructed FOV (reconstructed field of view) containing the designated super-resolution process range by the reconstructing section 36 on an enlarged scale are determined by the system controller 29 or the super-resolution processing section 32 (S5). The reconstruction parameters are principally determined depending on clinical requirements such as the size of an object region. The reconstruction parameters include, in addition to the center position and the size (diameter or radius) of the reconstructed FOV, an enlargement ratio, a reconstruction function, a reconstruction matrix, a slice pitch, etc. The enlargement ratio is determined so that a gentle PSF curve can be expressed. For example, when the reconstructed FOV is formed of a 512- by 512-pixel matrix, the enlargement ratio is set to three times or more, preferably, eight times as much as the reconstructed FOV.

Figure 3C:
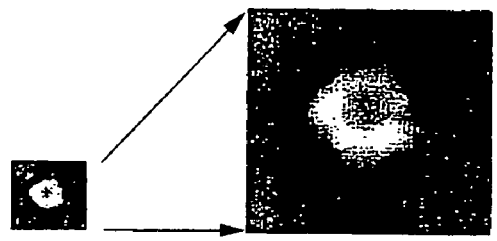

When the reconstruction parameters have been determined, the reconstruction parameters are sent automatically to the reconstructing section 36 under the control of the system controller 29 (S6). The reconstructing section 36 activates reconstruction batch processing by the control of the system controller 29 (S7). Thus an image of the reconstructed FOV containing a super-resolution process range is generated at the maximum special resolution of an X-ray CT scanner (refer to FIG. 3C). Since enlarged reconstruction is limited to the process range, super-resolution processing is applied to an image with the maximum special resolution of an X-ray CT scanner, thus improving the effective performance of super-resolution processing to increase the practical performance.

Figure 3D:
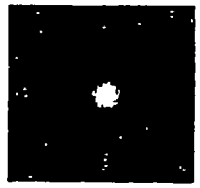

The image data reconstructed on an enlarged scale is sent from the reconstructing section 36 to the super-resolution processing section 32 by the control of the system controller 29 (S8) and is subjected to super-resolution processing (S9). The PSF data is first sent from the PSF storage section 31 to the super-resolution processing section 32 and stored in a storage section in the super-resolution processing section 32 together with data of the reconstructed image on an enlarged scale. When the resolution of the stored PSF data (image data of the reconstructed wire phantom on an enlarged scale) is different from the resolution of the enlarged image in step S7, the PSF is resampled by the super-resolution processing section 32 or the image processing section 33 to make it equal to that of the resolution of the image enlarged in step S7. FIG. 3D shows the resampled PSF.

In the super-resolution processing section 32, the image of the super-resolution process range is resolved at super resolution using the resampled two-dimensional (X and Y) PSF as necessary (S9). In the super-resolution processing, an image M in the super-resolution process range is deconvoluted (*) by PSF as follows:

$TM=M(*)PSF$

By the deconvolution, the resolution of the image in the super-resolution process range is increased. In this embodiment, an approximate solution is obtained by an iterative method, typically, Jacobi method to increase the accuracy to a true value. Although the iterative method requires an initial solution, a deconvoluted image TM is adopted as the initial solution. The initial solution may be a null image in place of the deconvoluted image TM. Initially, O=TM holds, where E is an error, * is deconvolution, and O is a solution. Then the following expression holds:

$E=(M-PSF*O)^2$

When a corrected vector dE/d0 is obtained from the gradient of E so as to minimize the error E, the expression is as follows:

$O_{N+1}=O_N-a*dE/d0$ where a is a constant.

Figure 3E:
Figure 10A:
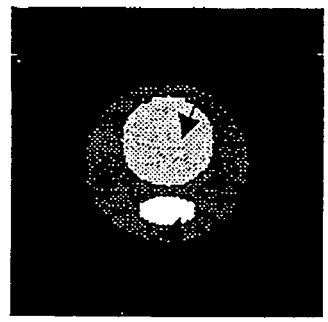
FIGS. 10A to 10C show an image subjected to the super-resolution processing according to the embodiment.
Figure 10B:
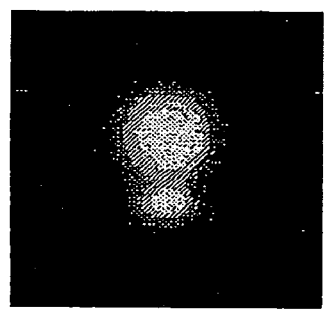
Figure 10C:
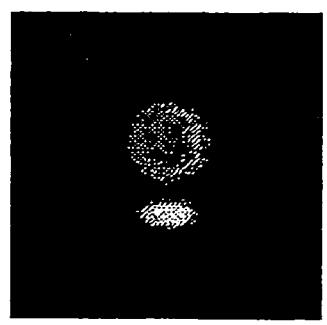
Figure 11:
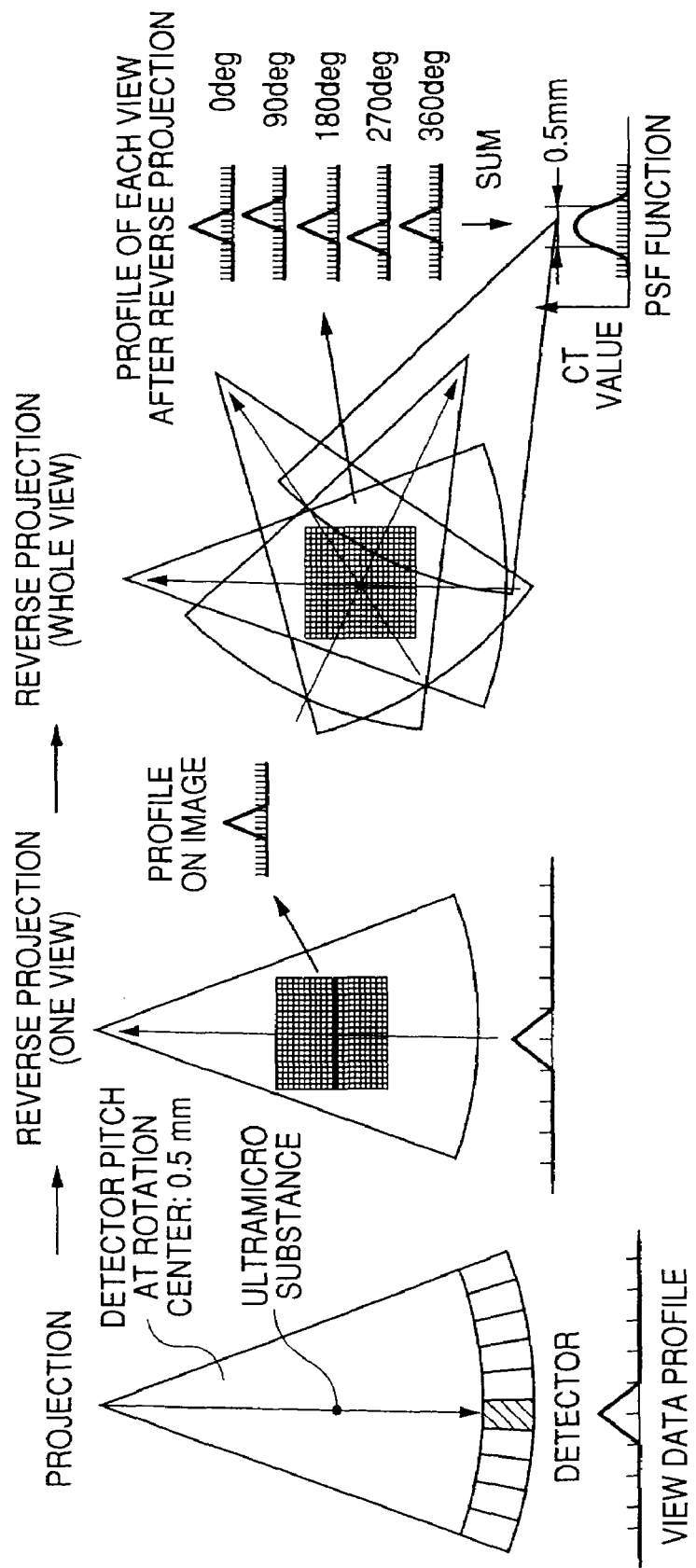
FIG. 11 is a diagram of the principle of the occurrence of blurring in a CT image.

An image having a resolution higher than the resolution (detecting element pitch) of the X-ray detector 23 is displayed on the display 38 as shown in FIG. 3E (S10). FIGS. 10A to 10C show the result of simulation. A mimic blood vessel (the true-value image in FIG. 10A) in which lime is attached to the inner wall is defined, which is convoluted by PSF to form a simulated out-of-focus measurement image (FIG. 10B). The measurement image is subjected to super-resolution processing, so that resolution increases to allow the blood vessel to be discriminated from the lime, as shown in FIG. 10C.

Figure 5A:
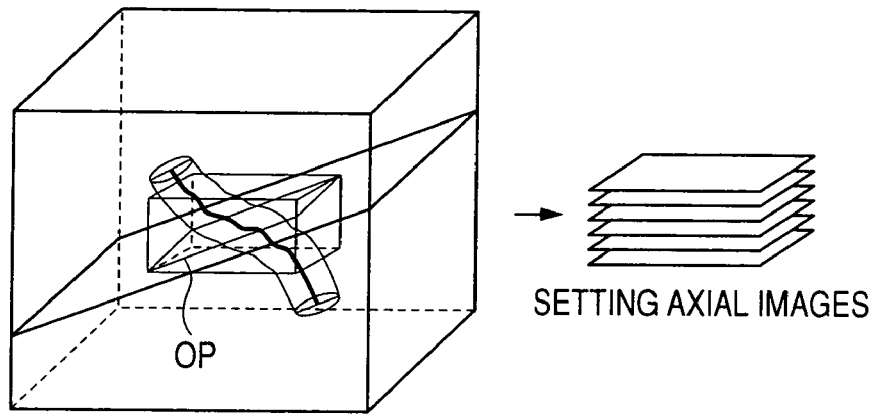
FIGS. 5A to 5D are supplementary diagrams of the second super-resolution processing procedure of FIG. 4.

Referring now to FIG. 4, the second super-resolution processing procedure will be described. In the first super-resolution process, the process range is defined on a reconstructed plane, or an axial plane perpendicular to Z-axis; in the second super-resolution process, the process range is set on a plane oblique relative to Z-axis, a so-called oblique plane. In step S11, a reference image is formed from volume data by the image processing section 33 under the control of the system controller 29 and displayed on the display 38 (refer to FIG. 5A). When an oblique plane OP oblique to Z-axis and a super-resolution process range thereon are designated on the displayed reference image by the operator with the input unit 39 (S12), multiple axial planes (XY planes) are set at minute intervals by the image processing section 33 such that they cross the process range on the designated oblique plane (S13). The minute intervals between the axial planes are set so as to express a gentle PSF curve with respect to Z-axis. For example, when the axial image has a slice thickness of 0.5 mm, the intervals between the axial planes are set one-fourth or less.

Figure 5B:
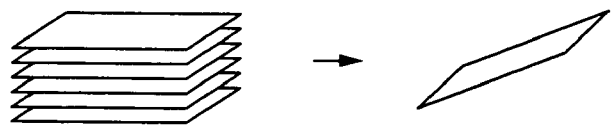

As in the first super-resolution process of steps S5 and S6, reconstruction parameters for reconstructing (zooming) the images of the multiple axial planes on an enlarged scale by the reconstructing section 36 are determined by the system controller 29 or the super-resolution processing section 32. The reconstruction parameters are sent to the reconstructing section 36 by the control of the system controller 29, where reconstruction batch processing is activated by the control of the system controller 29 (S14). Thus multiple images (a set of axial images) of the multiple axial planes are formed. The multiple image data is sent from the reconstructing section 36 to the image processing section 33 by the control of the system controller 29. As shown in FIG. 5B, an object image on the oblique plane is formed from the multiple images by multiplanar reformatting (MPR) (S15).

Figure 5C:
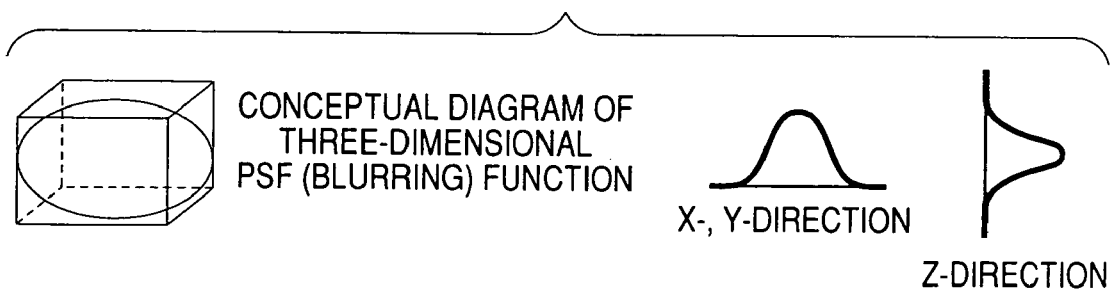
Figure 5D:

The three-dimensional PSF data illustrated in FIG. 5C is sent from the PSF storage section 31 to the super-resolution processing section 32, where it is stored in the storage section in the super-resolution processing section 32 together with the data of the image on the oblique plane. As shown in FIG. 5D, in the super-resolution processing section 32, a two-dimensional PSF on the oblique plane OP is formed from the stored three-dimensional PSF data (enlarged microsphere image data) (S16). The image on the oblique plane is subjected to super-resolution processing with the PSF of the formed oblique plane, as in the first super-resolution processing in step S9, (S17) and is displayed (S18).

Figure 6:
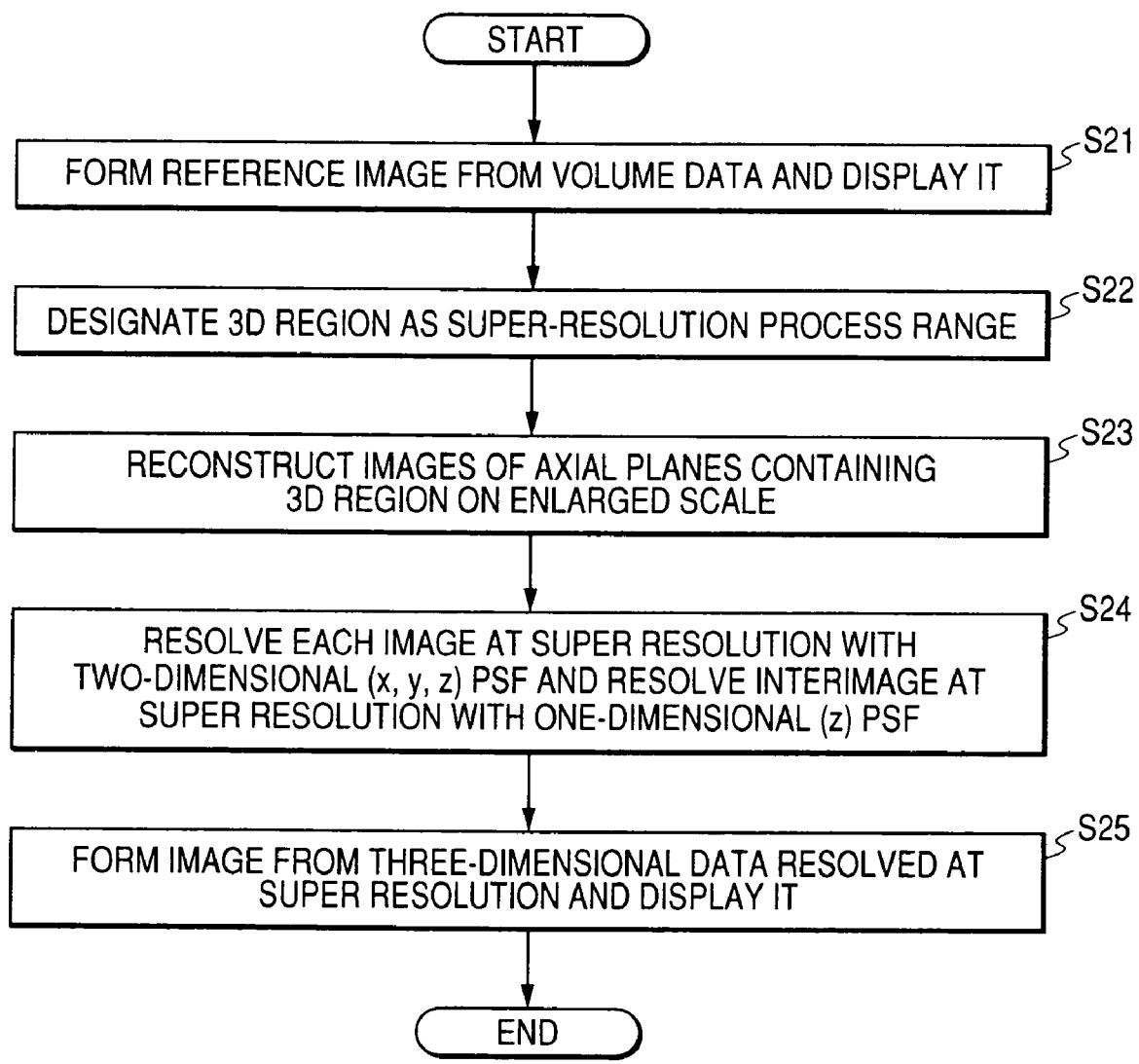
FIG. 6 is a flowchart for a third super-resolution processing procedure according to the embodiment.
Figure 7A:
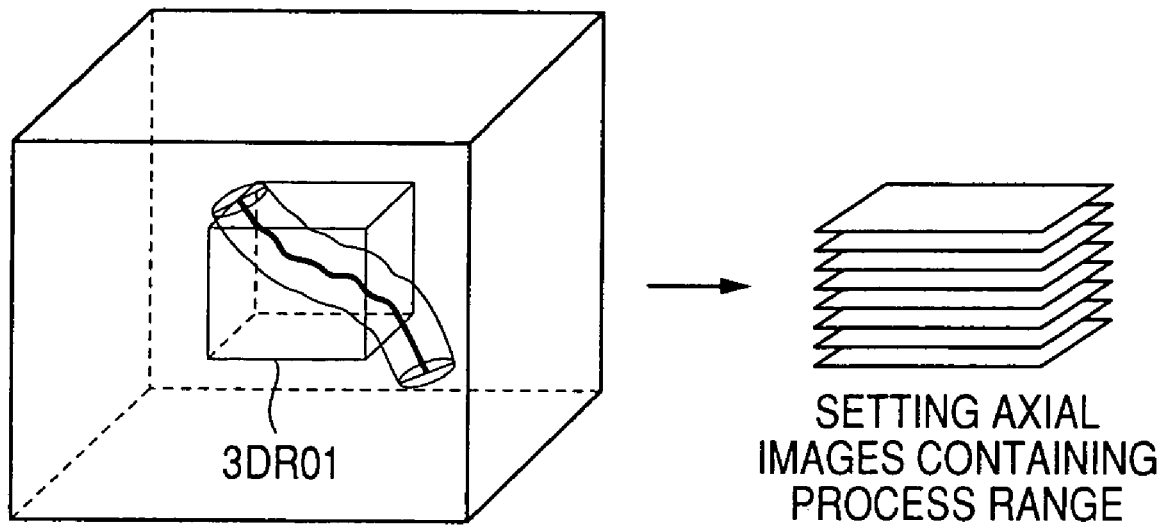
FIGS. 7A and 7B are supplementary diagrams of the third super-resolution processing procedure of FIG. 6.
Figure 7B:
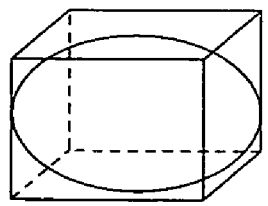

Referring to FIG. 6, the third super-resolution processing procedure will be described. In the first and second super-resolution processes, the process range is defined in two dimensions on the axial or oblique plane, and so a two-dimensional image is subjected to super-resolution processing. On the other hand, in the third super-resolution processing, the process range is defined in three dimensions, and so a three-dimensional image is subjected to super-resolution processing. In step S21, a reference image is formed from volume data by the image processing section 33 and displayed on the display 38 (refer to FIG. 7A) under the control of the system controller 29. When a three-dimensional process range 3D-ROI is designated on the displayed reference image by an operator with the input unit 39 (S22), multiple axial planes (XY planes) contained in the designated three-dimensional process range 3D-ROI are set at minute intervals by the image processing section 33. The minute intervals between the axial planes are set so that a gentle PSF curve can be expressed with respect to Z-axis. Reconstruction parameters for reconstructing (zooming) the enlarged images on the set multiple axial planes by the reconstructing section 36 are determined by the system controller 29 or the super-resolution processing section 32. The reconstruction parameters are sent to the reconstructing section 36 by the control of the system controller 29, wherein reconstruction batch processing is activated by the control of the system controller 29 (S23). Thus multiple images of the multiple axial planes (a set of axial images) are formed. The data of the multiple images are sent to the super-resolution processing section 32 together with the data of three-dimensional PSF (FIG. 7B) in the PSF storage section 31 by the control of the system controller 29. In the super-resolution processing section 32, the multiple images on the multiple axial planes are subjected to super-resolution processing with the three-dimensional PSF data (enlarged microsphere image data) (S24) and are displayed (S25).

Although the oblique-plane super resolution is performed in such a sequence that the multiple axial planes are reconstructed on an enlarged scale, an oblique image is formed on an oblique plane from the enlarged multiple axial images by multiplanar reformatting, and the oblique image is subjected to super-resolution processing, other sequences are possible. For example, it is also possible to perform the super resolution of an oblique plane in such a sequence that the multiple axial planes are reconstructed on an enlarged scale, the enlarged axial planes are each subjected to super resolution, and then an oblique image is formed on an oblique plane from the multiple super-resolution axial images by multiplanar reformatting.

An application of the super resolution by the super-resolution processing section 32 will now be described. Here a method for improving the convergence of iterative solution and the accuracy of images of super resolution will be described. As well known, an example of the CT value of each region in coronary-artery CT inspection is as follows:

Blood Vessel: 60 HU

Blood (contrast medium): 200 to 300 HU

Fat: −80 to −50 HU

Stent: 500 UH or more

Figure 8:
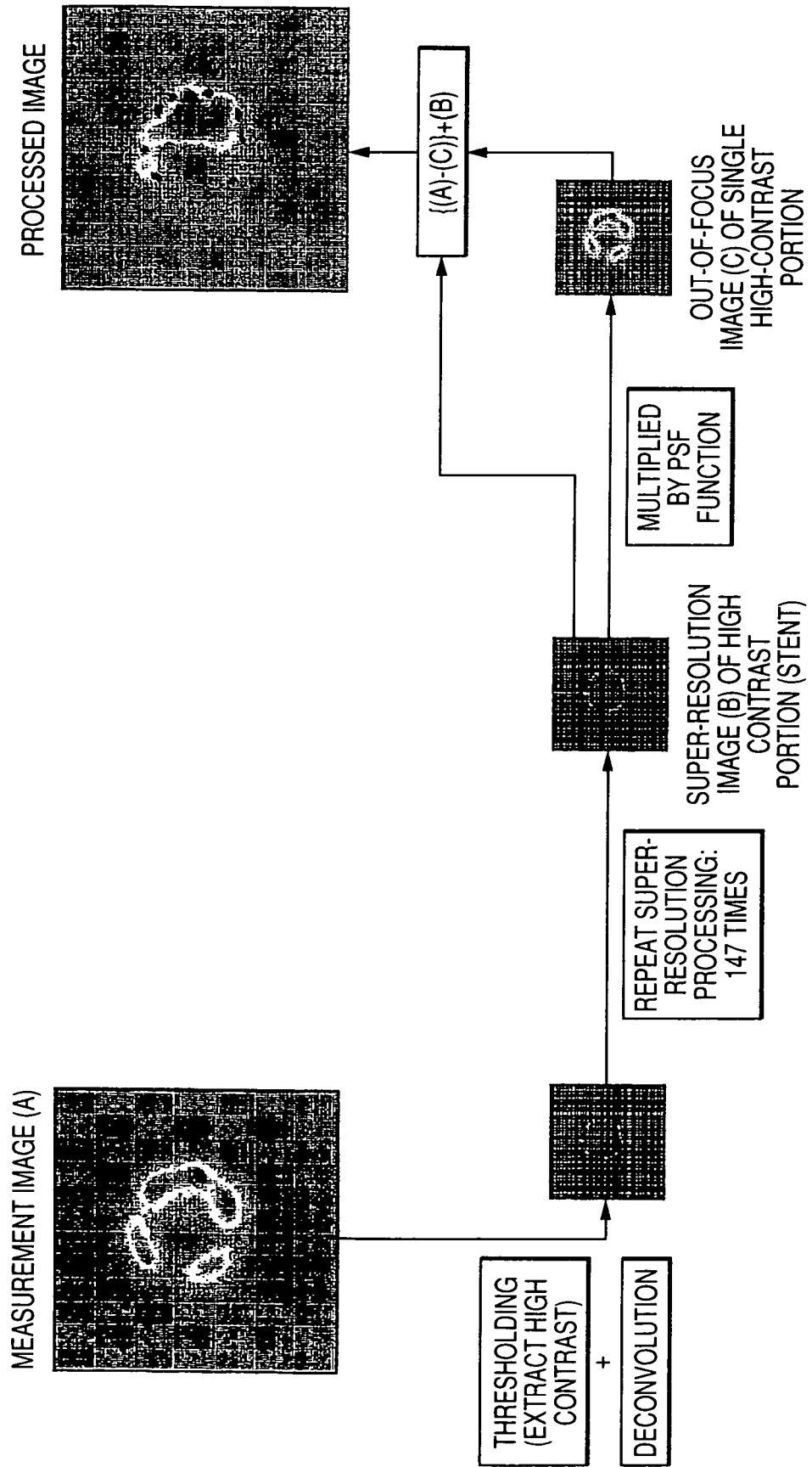
FIG. 8 is a diagram of an application of the super-resolution processing according to the embodiment.

Particularly, a stent has such a high CT value that it is greatly influenced by blurring and takes a large number of iterations for convergence because of its large value. On the other hand, the other tissues have so low CT values that they are likely to be affected by image noise. Therefore, a large number of iterations as in the stent tend to cause no convergence but cause divergence. Accordingly, it is effective to perform iteration, with a high-contrast portion, such as a stent and a low-contrast portion under different conversion conditions or separated. Referring to FIG. 8, when a measurement image (A) contains a mixture of a substance of a high CT value, such as a stent, and a substance of a low CT value, such as a blood vessel, fat, or cardiac muscle, the image of the stent and its surroundings are first extracted from the image. In other words, a low-contrast portion is removed from the measurement image by thresholding and a high-contrast portion is extracted together with its surroundings. For example, a portion within the radius of PSF function is extracted as surroundings from each high-contrast pixel that is extracted by thresholding. To pixels that are not extracted, the minimum pixel value in the measurement image or the threshold used in the thresholding is given as pixel values. The image whose high-contrast portion and surroundings are extracted is deconvoluted by PSF under a specified constraint that, for example, the minimum pixel value or values smaller than the threshold are not permitted, and then an iterative method is applied, e.g., 147 times with it as the initial solution. Thus a super-resolution image (B) having only a high-contrast portion (a stent in this case) is formed.

Then the super-resolution image (B) having only a high-contrast portion is convoluted by PSF to form an out-of-focus image (C) having only a high-contrast portion. The out-of-focus image (C) having only a high-contrast portion is subtracted from the measurement image (A) to form an image (D) having only a low-contrast portion and then the image (D) having only a low-contrast portion is displayed in combination with the super-resolution image (B) having only a high-contrast portion. Thus, a high-contrast super-resolution image can be acquired at high accuracy without the influence of the low-contrast portion and, at the same time, the image of the low-contrast portion can be separated from the high-contrast portion.

Figure 9:
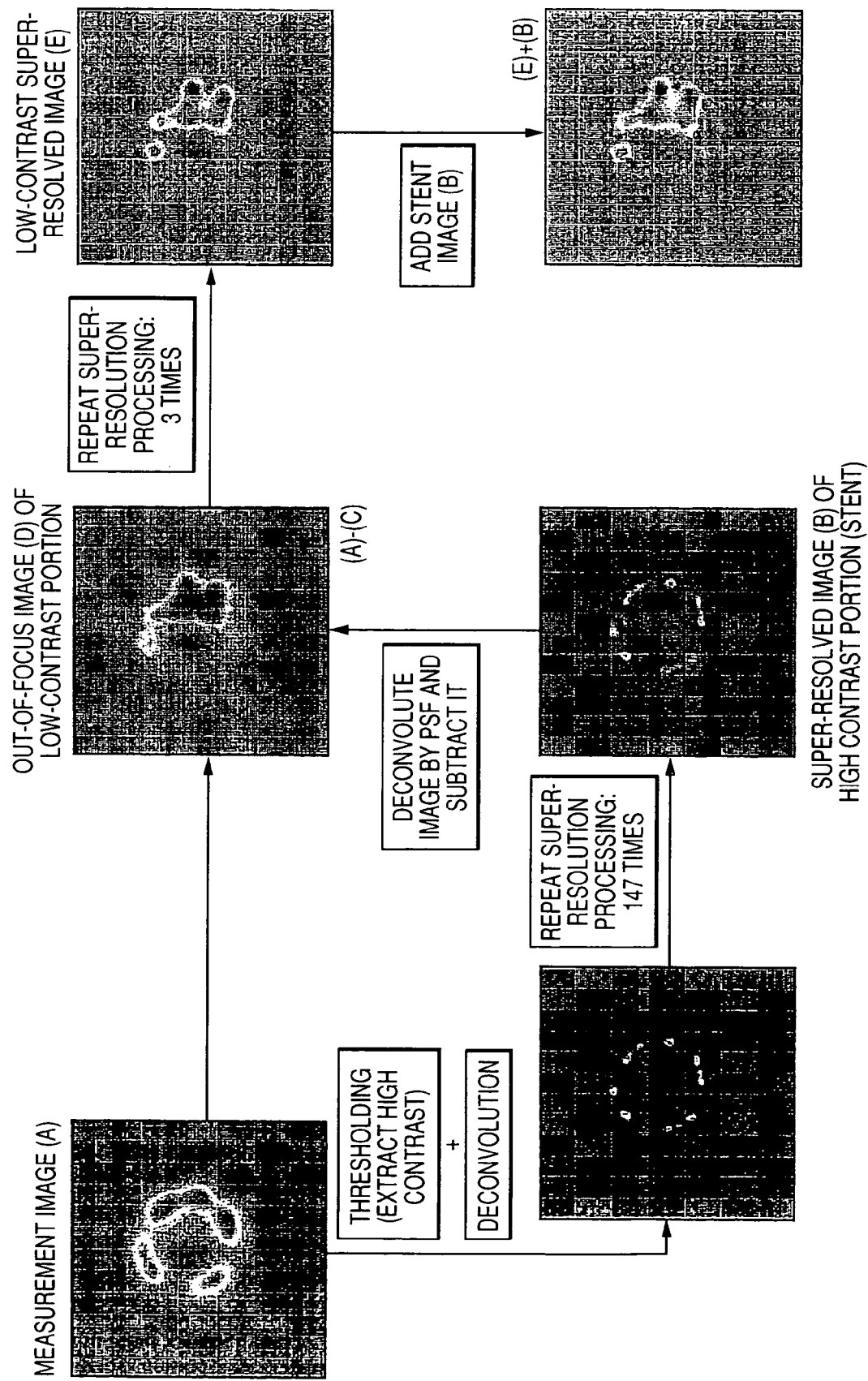
FIG. 9 is a diagram of another application of the super-resolution processing according to the embodiment.

Referring to FIG. 9, it is also possible that the out-of-focus image (D) having only a low-contrast portion formed by subtracting the out-of-focus image (C) having only a high-contrast portion from the measurement image (A) is subjected to super-resolution processing to form a low-contrast super-resolution image (E) and display it in combination with the high-contrast super-resolution image (B).

Since the high-contrast portion and the low-contrast portion are separately subjected to super-resolution processing in that way, the convergence of iterative solution and the accuracy of images in super-resolution processing can be improved.

When the spatial frequency of an image to be resolved at super resolution becomes higher than a required resolution, the convergence is decreased in the iterative method, as in the foregoing. Therefore it is necessary to limit the recovery band to prevent divergence. Thus, band limitation (low-pass in frequency space) is performed so that the initial solution does not contain a more high-frequency component than is necessary.

$$O_1 = M(*)PSF*F$$

where F is a bandlimiting filter.

Each correction vector is subjected to band limitation so that a more high-frequency component than is necessary is not contained in the iterative method.

$$O_{N+1} = O_N - a*dE/dx*F$$

In a two-step iterative method A), a high-resolution stent image is first obtained with a high-frequency component left by reduced band limitation for a stent. Then, in the second iterative solution, the image of a blood vessel etc. is recovered by strong band limitation with the high-resolution stent image as the initial solution.

$$O' = M(*)PSF*F_1$$

where $F_1$ is a filter that passes a high-frequency component relatively well.

$$O_{N+1} = O_N - a*dE/dx*F_1$$

Upon convergence, the bandlimiting filter is replaced and iteration is performed again using $O_{N+1}$ as an initial solution.

$$_{N+1,2} = O_{N2} - a*dE/dx*F_2$$

where $F_2$ is a filter that passes a high-frequency component little.

Thus, since in the second iteration the correction vector contains no high-frequency component and stores the high-frequency component of the last solution $O_{N+1}$ of the first iteration, the stent image is stored. On the other hand, since the second iterative solution $O_{N+1,2}$ contains no high-frequency component other than the stent image, convergence is maintained.

When the iterative solution is repeated many times, the influence of image noise increases to make solution easy to diverge. Accordingly, it is also important to give constraints depending on the pixel value of the image, thereby improving convergence conditions.

Pixel values exceeding a specified range are converted to a fixed value. The correction amount is limited with the CT value of each pixel of the measurement image as reference. A specified allowable variation range is determined from each CT value of the measurement image and each iterative solution value is subjected to clipping. The allowance range may differ from one pixel of the measurement image to another.

$$\text{iterative solution } O_{N+1} = CLIP(O_N - a*dE/dx)$$

where CLIP( ) is a clipping function.

Example: When the value of a pixel of a measurement image 0 is 50 HU, the value of the pixel of iterative solution of 0 HU or less is clipped off to 0 HU and the value of 100 HU or more is clipped off to 100 HU.

The object of a minute size and a high CT value, such as a stent, varies in the pixel value considerably due to recovery, so that it is difficult to set the allowance range. Accordingly, only pixels may be clipped off for objects of a low CT value, such as blood vessels and blood.

Alternatively, a specified allowable variation range may be determined from each pixel CT value of the measurement image and each iterative solution may be subjected to clipping. The allowance range may differ from one pixel of the measurement range to another.

$$\text{correction value } O_{N+1} = O_N - CLIP(a*dE/dx)$$

Example: When the value of a pixel of a measurement image 0 is 50 HU, the allowance correction value of one iteration is set to 5 HU. Alternatively, a gradient vector may be obtained for the pixel on the measurement image, wherein a large allowance correction value is set at a steep gradient, while a small allowance correction value is set at a gentle gradient.

The constraints and iterative algorisms other than Jacobi method may be combined.

Additional advantages and modifications will readily occur to those skilled in the art. Therefore, the invention in its broader aspects is not limited to the specific details and representative embodiments shown and described therein. Accordingly, various modifications may be made without departing from the spirit or scope of the general inventive concept as defined by the appended claims and their equivalents.

What is claimed is:

1. A super-resolution processor, comprising:
    a storage unit configured to store projection data of a sample acquired by an X-ray CT scanner;
    a designation unit configured to designate a super-resolution process range on a three-dimensional image of the sample;
    an image reconstruction unit configured to reconstruct image data from the projection data only in the designated super-resolution process range; and
    a super-resolution processing unit configured to perform super resolution of the reconstructed image data using point spread functions for the X-ray CT scanner.

2. The super-resolution processor according to claim 1, wherein the super-resolution processing unit performs a process of deconvoluting the image data by the stored point spread functions.

3. The super-resolution processor according to claim 2, wherein the super-resolution processing unit performs a process of iteration for minimizing errors between the image data and the deconvoluted image data that is used as the initial solution.

4. The super-resolution processor according to claim 1, further comprising:
    a reconstructing-condition determination unit configured to determine reconstruction conditions based on the super-resolution process range.

5. The super-resolution processor according to claim 4, wherein the diameter of the reconstructed field of view is at most one-third of that of the photographing field of view of the projection data.

6. The super-resolution processor according to claim 1, wherein a high contrast portion of the image is extracted by thresholding and super-resolution is performed on the extracted high contrast portion.

7. The super-resolution processor according to claim 1, wherein an out-of-focus image having only a high-contrast portion is subtracted from the three-dimensional image of the sample and a result of the subtraction is displayed with a super-resolution image having only a high-contrast portion.

8. A medical diagnostic imaging apparatus, comprising:
- an image acquisition unit configured to acquire medical image data from a sample;
- a designation unit configured to designate a super-resolution process range on a three-dimensional image of the sample; and
- a super-resolution processing unit configured to perform super resolution of the medical image data using point spread functions for the image acquisition unit only in the designated super-resolution process range.

9. The medical diagnostic imaging apparatus according to claim 8, wherein the super-resolution processing unit performs a process of deconvoluting the image data by the stored point spread functions.

10. The medical diagnostic imaging apparatus according to claim 9, wherein the super-resolution processing unit performs a process of iteration for minimizing errors between the image data and the deconvoluted image data that is used as the initial solution.

11. The medical diagnostic imaging apparatus according to claim 8, further comprising:
- a reconstructing-condition determination unit configured to determine reconstruction conditions base based on the super-resolution process range.

12. The medical diagnostic imaging apparatus according to claim 11, wherein the diameter of the reconstructed field of view is at most one-third of that of the photographing field of view of the projection data.

* * * * *